United States Patent [19]

Kaduk

[11] 4,323,481
[45] Apr. 6, 1982

[54] SYNTHESIS OF MOLECULAR SIEVES USING BETA-DIKETONES AS ORGANIC TEMPLATES

[75] Inventor: James A. Kaduk, Naperville, Ill.

[73] Assignee: Standard Oil Company (Indiana), Chicago, Ill.

[21] Appl. No.: 238,592

[22] Filed: Feb. 26, 1981

[51] Int. Cl.³ .................. C01B 33/28; B01J 29/06
[52] U.S. Cl. .................. 252/455 Z; 260/448 C; 423/329
[58] Field of Search .................. 423/328–330; 252/431 R, 455 Z; 260/448 C

[56] References Cited

U.S. PATENT DOCUMENTS

| | | | |
|---|---|---|---|
| 3,933,974 | 1/1976 | Winquist | 423/329 |
| 3,966,883 | 6/1976 | Vaughan et al. | 423/329 |
| 4,000,248 | 12/1976 | Martin | 423/328 X |
| 4,016,245 | 4/1977 | Plank et al. | 423/328 |
| 4,046,859 | 9/1977 | Plank et al. | 423/329 |
| 4,107,195 | 8/1978 | Rollmann | 423/329 |
| 4,139,600 | 2/1979 | Rollmann | 423/329 |
| 4,205,052 | 5/1980 | Rollmann | 423/329 |
| 4,251,499 | 2/1981 | Nanne et al. | 423/329 |

*Primary Examiner*—Edward J. Meros
*Attorney, Agent, or Firm*—Wallace L. Oliver; William H. Magidson; William T. McClain

[57] ABSTRACT

A ferrierite crystalline aluminosilicate is prepared by (1) forming an aqueous mixture of an oxide of aluminum, an oxide of silicon, a metal cation and a beta-diketone as a template compound, (2) maintaining the pH of such mixture between 9 and 14, and (3) crystallizing the mixture.

21 Claims, No Drawings

SYNTHESIS OF MOLECULAR SIEVES USING BETA-DIKETONES AS ORGANIC TEMPLATES

BACKGROUND OF THE INVENTION

This invention relates to a new method of preparing crystalline molecular sieve compositions.

Zeolitic materials, both natural and synthetic, are known to have catalytic capabilities for many hydrocarbon processes. Zeolitic materials typically are ordered porous aluminosilicates having a definite structure with cavities interconnected by channels. The cavities and channels throughout the crystalline material generally are uniform in size allowing selective separation of hydrocarbons. Consequently, these materials in many instances are known in the art as "molecular sieves" and are used, in addition to selective adsorptive processes, for certain catalytic properties. The catalytic properties of these materials are affected to some extent by the size of the molecules which selectively penetrate the crystal structure, presumably to contact active catalytic sites within the ordered structure of these materials.

Generally, the term "molecular sieve" includes a wide variety of both natural and synthetic cation-containing crystalline zeolite materials. They generally are characterized as crystalline aluminosilicates which comprises networks of $SiO_4$ and $AlO_4$ tetrahedra in which silicon and aluminum atoms are cross-linked by sharing of oxygen atoms. The negative framework charge resulting from the substitution of an aluminum atom for a silicon atom is balanced by cations, for example, alkali-metal or alkaline-earth-metal cations, ammonium ions, or hydrogen ions.

Prior art developments have resulted in the formations of many synthetic zeolitic crystalline materials. Crystalline aluminosilicates are the most prevalent and, as described in the patent literature and in the published journals, are designated by letters or other convenient symbols. Examples of these materials are Zeolite A (U.S. Pat. No. 2,882,243), Zeolite X (U.S. Pat. No. 2,882,244), Zeolite Y (U.S. Pat. No. 3,130,007), Zeolite ZSM-4 (U.S. Pat. No. 3,578,723), Zeolite ZSM-5 (U.S. Pat. No. 3,702,886), Zeolite ZSM-11 (U.S. Pat. No. 3,709,979), Zeolite ZSM-12 (U.S. Pat. No. 3,832,449), Zeolite NU-1 (U.S. Pat. No. 4,060,590) and others.

Molecular sieves characterized as "ferrierite" by a combination of chemical composition and X-ray diffraction spectra are known as naturally occurring materials and as synthesized materials. For example, a conventional ferrierite sieve is produced by crystallizing a basic mixture of sodium aluminate and an oxide of silicon without the use of an organic template compound. Such ferrierites are described in D. W. Breck "Zeolite Molecular Sieves," John Wiley & Sons, 1974, incorporated by reference herein. U.S. Pat. No. 4,000,248 discloses a method of producing a ferrierite molecular sieve using N-methyl pyridinium hydroxide as an organic template compound in the crystallization of the sieve. U.S. Pat. Nos. 4,016,245, 4,107,195 and 4,046,859 disclose formation of a ferrierite-like material using an organic template derived from ethylenediamine, pyrrolidine or butanediamine or organometallic 2-(hydroxyalkyl)trialkylaluminum compounds. The present invention is a new method of preparing a ferrierite molecular sieve using simple organic compounds as templates in which silicon/aluminum (Si/Al) ratio (or as expressed as oxides, the silica/alumina ($SiO_2/Al_2O_3$) ratio) can be adjusted to effect better selectivity in hydrocarbon conversion reactions.

SUMMARY OF THE INVENTION

What has been discovered is a method to prepare a ferrierite crystalline aluminosilicate comprising (1) forming an aqueous mixture of an oxide of aluminum, an oxide of silicon, a metal cation and a beta-diketone, (2) maintaining the pH of such mixture between 11 and 14, and (3) crystallizing the mixture.

BRIEF DESCRIPTION OF THE INVENTION

The present invention is a method of producing a crystalline molecular sieve, preferably ferrierite-like, using a beta-diketone, preferably 2,4-pentanedione, as a template.

A ferrierite sieve is characterized as a crystalline aluminosilicate having the following chemical composition in terms of oxides:

$$0.9 \pm 0.2\ M_{2/n}O:Al_2O_3:ySiO_2:z\ H_2O$$

wherein M is at least one cation of valence n, y is between about 2 and about 150, preferably between about 6 and about 50, and z is between 0 and about 200, preferably between 0 and 120. The X-ray diffraction pattern of a typical ferrierite (obtained from material prepared in Example I) is given in Table I.

Alternatively, a ferrierite sieve can be characterized as a crystalline aluminosilicate having the unit cell formula:

$$M^{n+}{}_{1.0 \pm 0.2\ (w/n)}Al_wSi_{36-w}O_{72} \cdot xH_2O$$

wherein M is at least one cation of valence n, w is between about 0.5 and about 18, preferably between about 1 and about 7 and most preferably between about 2 and about 5, and x is between 0 and about 50 and preferably between 0 and about 30.

The X-ray powder diffraction measurements shown in Table I were obtained on a Phillips diffractometer using copper K alpha radiation in conjunction with an AMR focusing monochromometer and a theta angle compensating slit in which aperture varies with theta angle. Data generated by the diffractometer were processed through a Canberra hardware/software package and presented in a strip chart and in a numerical printout of relative intensity (peak height), interplanar spacing and two-theta angle. The compensating slit and the Canberra package tend to increase the peak-to-background ratios while reducing the peak intensities at low theta angles [large interplanar spacings] and increasing the peak intensities at high theta angles [small interplanar spacings].

In reporting the results obtained, relative intensities, i.e., relative peak heights, were arbitrarily assigned the following values:

| Relative Peak Height | Assigned Strength |
| --- | --- |
| less than 10 | VW (very weak) |
| 10-19 | W (weak) |
| 20-39 | M (medium) |
| 40-69 | MS (medium strong) |
| 70-89 | S (strong) |
| greater than 90 | VS (very strong) |

Interplanar spacings are represented by "d" and are expressed in terms of Angstrom units (A) and nanometers (nm).

TABLE I

| d-Spacing | | I/Io | Assigned Strength |
|---|---|---|---|
| A | nm | | |
| 9.30 | 0.930 | 78 | S |
| 6.96 | 0.696 | 31 | M |
| 6.86 | 0.686 | 31 | M |
| 6.51 | 0.651 | 25 | M |
| 5.68 | 0.568 | 11 | W |
| 5.60 | 0.560 | 13 | W |
| 4.69 | 0.469 | 3 | VW |
| 3.95 | 0.395 | 66 | MS |
| 3.81 | 0.381 | 29 | M |
| 3.75 | 0.375 | 52 | MS |
| 3.63 | 0.363 | 28 | M |
| 3.52 | 0.352 | 100 | VS |
| 3.45 | 0.345 | 79 | S |
| 3.35 | 0.335 | 16 | W |
| 3.29 | 0.329 | 24 | M |
| 3.12 | 0.312 | 38 | M |
| 3.04 | 0.304 | 23 | M |
| 2.93 | 0.293 | 13 | W |
| 2.88 | 0.288 | 12 | W |
| 2.70 | 0.270 | 8 | VW |
| 2.63 | 0.263 | 10 | W |
| 2.56 | 0.256 | 7 | VW |
| 2.47 | 0.247 | 7 | VW |
| 2.40 | 0.240 | 8 | VW |
| 2.30 | 0.230 | 6 | VW |
| 2.25 | 0.225 | 5 | VW |
| 2.23 | 0.223 | 6 | VW |
| 2.17 | 0.217 | 3 | VW |
| 2.13 | 0.213 | 4 | VW |
| 2.11 | 0.211 | 5 | VW |
| 1.99 | 0.199 | 13 | W |
| 1.94 | 0.194 | 7 | VW |
| 1.92 | 0.192 | 12 | W |
| 1.86 | 0.186 | 10 | W |
| 1.83 | 0.183 | 3 | VW |
| 1.80 | 0.180 | 4 | VW |
| 1.77 | 0.177 | 10 | W |
| 1.73 | 0.173 | 3 | VW |
| 1.70 | 0.170 | 3 | VW |
| 1.65 | 0.165 | 4 | VW |
| 1.60 | 0.160 | 3 | VW |

The ferrierite molecular sieve of this invention is prepared by crystallizing an aqueous mixture, at a controlled pH, of a source of cations, an oxide of aluminum, an oxide of silicon, and a beta-diketone as a template compound.

Typically, the mole ratios of the various reactants can be varied to produce the crystalline aluminosilicates of this invention. Specifically, the mole ratios of the initial reactant concentrations are indicated below:

| | Broad | Preferred | Most Preferred |
|---|---|---|---|
| Si/Al | 1–120 | 5–40 | 6–11 |
| SiO$_2$/Al$_2$O$_3$ | 2–240 | 10–80 | 12–22 |
| R/Si | 0.01–1.0 | 0.1–0.5 | 0.15–0.35 |
| M$^{n+}$/Al | 0.1–100 | 1–10 | 2–5 |
| R/Al | 0.01–120 | 0.5–20 | 1–4 |
| H$_2$O/Si | 5–100 | 10–40 | 15–25 | wherein R is an organic compound and M is at least one cation having a valence n, such as an alkali-metal or an alkaline-earth-metal cation.

By regulation of the quantity of aluminum in the reaction mixture, it is possible to vary the silicon-/aluminum molar ratio in the final product in a range of from about 2 to about 150 and preferably from about 6 to about 50 and most preferably about 8–12. Production of ferrierite can be promoted by seeding with a small amount of crystalline ferrierite. Generally, at least about 85 wt.% of the aluminum present in a crystallization mixture is incorporated into a crystalline aluminosilicate product.

By decreasing the silicon/aluminum ratio and increasing the digestion time of the crystallizing mixture a molecular sieve in the mordenite crystalline form can be prepared. Typically, a mordenite can form if the Si/Al ratio in the crystallizing mixture is about 4 to about 20 and more typically about 6 to about 16. Catalysts made from these mordenites have some hydrocarbon conversion activity, but generally have lower activity than similarly prepared ferrieriter-based catalysts.

More specifically, the ferrierite material of the present invention is prepared by mixing a cation source compound, an aluminum oxide source, and an organic template compound in water (preferably distilled or deionized). The order of addition usually is not critical although a typical procedure is to dissolve sodium hydroxide and sodium aluminate in water and then add the template compound. Generally, after adjusting the pH, the silicon oxide compound is added with intensive mixing such as that performed in a Waring Blender. After the pH again is checked and adjusted, the resulting slurry is transferred to a stirred, closed crystallization vessel for a suitable time. After crystallization, the resulting crystalline product can be filtered, washed with water, dried, and calcined.

During preparation, acidic conditions should be avoided. When alkali metal hydroxides are used, the pH of the system should broadly fall within the range of about 11 to about 14. Advantageously, the pH of the reaction system falls within the range of about 12.3 to about 13.0, and most preferably between about 12.4 to about 12.8.

Examples of oxides of silicon useful in this invention include silicic acid, sodium silicate, tetraalkyl silicates and Ludox, a stabilized polymer of silicic acid manufactured by E. I. du Pont de Nemours & Co. Typically, the oxide of aluminum source is sodium aluminate although equivalent species can be used such as a mixture of sodium hydroxide and aluminum sulfate.

Useful cations in this invention include alkali-metal and alkaline-earth-metal cations such as sodium, potassium, calcium and magnesium. Ammonium cations may be used in conjunction with such metal cations. Since basic conditions are required for crystallization of the molecular sieve of this invention, the source of such cation usually is a hydroxide such as sodium hydroxide.

Generally, corresponding germanium compounds can be substituted for the silicon oxides and corresponding gallium compounds can be substituted for the aluminates as described herein.

Organic templates useful in this invention are beta-diketones of the structure:

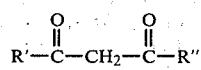

wherein R' and R" are hydrocarbon or substituted hydrocarbon radicals containing one to about 10 carbon atoms. The preferable template useful in this invention is 2,4-pentanedione. It is believed that under basic conditions the beta-diketones useful as templates in this invention are in a diketonate form which complexes with aluminum atoms during crystallization.

In a more detailed description of a typical preparation of this invention, suitable quantities of sodium hydroxide and sodium aluminate are dissolved in distilled or deionized water followed by addition of the organic template. Preferably, the pH is adjusted between 12.5 and 13, and most preferably between about 12.6 and about 12.8, using a compatible base or acid such as sodium bicarbonate or sodium hydroxide. A lower pH favors production of amorphous material while a higher pH favors production of a mordenite-like sieve. After sufficient quantities of silicic acid polymer (Ludox) are added with intensive mixing, preferably the pH is again checked and adjusted to a range of about 12.3 to 13.0, preferably about 12.4 to 12.8. The resulting slurry is transferred to a closed crystallization vessel and moderately stirred usually at a pressure at least the vapor pressure of water for a time sufficient to permit crystallization which usually is about 0.25 to about 20 days, typically is about one to about ten days and preferably is about two to about five days, at a temperature ranging from about 100° to about 250° C., preferably about 125° to about 200° C. Preferably, the crystallization temperature is maintained below the decomposition temperature of the organic template compound. Especially preferred conditions are stirring at about 165° C. for about three days. Samples of material can be removed during crystallization to check the degree of crystallization and determine the optimum crystallization time. If the crystallizing mixture is permitted to digest too long, a typically inactive mordenite will form.

The crystalline material formed can be separated and recovered by well-known means such as filtration with washing. This material can be mildly dried for anywhere from a few hours to a few days at varying temperatures, typically about 50°-200° C., to form a dry cake which can then be crushed to a powder or to small particles and extruded, pelletized, or made into forms suitable for its intended use. Typically, materials prepared after mild drying contain organic template compound and water of hydration within the solid mass and a subsequent activation or calcination procedure is necessary, if it is desired to remove this material from the final product. Typically, mildly dried product is calcined at temperatures ranging from about 260° C. to about 850° C. and preferably about 525° to about 650° C. Extreme calcination temperatures or prolonged crystallization times may prove detrimental to the crystal structure or may totally destroy it. Generally, there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 600° C. is reached. Calcination at this temperature usually is continued for about four hours.

In contrast to naturally-occurring ferrierites which usually have Si/Al ratios of about 5, the zeolite of this invention typically has a Si/Al ratio of about 10, which indicates that there are about three to four aluminum atoms per unit cell. The zeolite of this invention typically shows more stability and greater selectivity in hydrocarbon conversions than natural ferrierite.

The ferrierite crystalline aluminosilicates prepared according to this invention can be used as catalysts or as adsorbents whether in the alkali-metal or alkaline-earth-metal forms, the ammonium form, the hydrogen form, or any other univalent or multivalent cationic form. Mixtures of cations may be employed.

A catalytically active material can be placed onto the aluminosilicate structure by ion exchange, impregnation, a combination thereof, or other suitable contact means. Advantageously, before placing a catalytically active metal ion or compound on the aluminosilicate structure, the aluminosilicate is in the hydrogen form which, typically, is produced by exchange with ammonium ion followed by calcination.

The original cation in the crystalline aluminosilicate prepared according to this invention, which usually is sodium ion, can be replaced by ion exchange with other cations including other metal ions and their amine complexes, alkylammonium ions, ammonium ions, hydrogen ions, and mixtures thereof. Preferred replacing cations are those which render the crystalline aluminosilicate catalytically active, especially for hydrocarbon conversion. Typical catalytically active ions include hydrogen, metal ions of Groups IB, IIB, IIIA and VIII, and of manganese, vanadium, chromium, uranium, and rare earth elements. Presence of sodium ion in a composition usually is detrimental to catalytic activity.

Also water soluble salts of catalytically active materials can be impregnated onto the crystalline aluminosilicate of this invention. Such catalytically active materials include hydrogen, metals of Groups IB, IIB, IIIA, IVB, VB, VIB, VIIB and VIII, and rare earth elements.

Ion exchange and impregnation techniques are well known in the art. Typically, an aqueous solution of a cationic species is exchanged one or more times at about 25° to about 100° C. Impregnation of a catalytically active compound on the aluminosilicate or on a composition comprising the crystalline aluminosilicate suspended in and distributed throughout a matrix of a support material such as a porous refractory inorganic oxide such as alumina, often results in a suitable catalytic composition.

The choice of catalytically active materials to be placed on the crystalline aluminosilicate depends on the intended process use. For example, for hydrocarbon conversion processes such as xylene isomerization and isomerization of ethylbenzene to xylenes, metal ions such as nickel ions and other Group VIII metal ions can be exchanged onto the crystalline aluminosilicate. Also, compounds of catalytically active metal compounds such as oxides of molybdenum, chromium and tungsten can be impregnated on the crystalline aluminosilicate prepared according to this invention. A combination of ion exchange and impregnation can be used.

The amount of catalytically active metal placed on the aluminosilicate of this invention can vary from less than one weight percent to about thirty weight percent, typically from about 0.05 to about 25 weight percent, depending on the process use intended. The optimum amount can be determined easily by routine experimentation.

If desired, a hydrogenating component, such as ions or compounds of tungsten, vanadium, molybdenum, rhenium, nickel, cobalt, chromium, manganese, a noble metal such as platinum or palladium, or a rare earth element, can be ion exchanged, impregnated or physically admixed with compositions prepared according to this invention.

The crystalline aluminosilicate prepared according to this invention may be incorporated as a pure material in a catalyst or adsorbent, or may be admixed with or incorporated within various binders or matrix materials depending upon the intended process use. The crystalline aluminosilicate can be combined with active or inactive materials, synthetic or naturally-occurring zeolites, as well as inorganic or organic materials which would be useful for binding the aluminosilicate. Well-known materials include silica, silica-alumina, alumina, alumina sols, hydrated aluminas, clays such as bentonite or kaolin, or other binders well known in the art. Typically, the aluminosilicate is incorporated within a matrix material by blending with a sol or gel of the matrix material and gelling the resulting mixture. Also, solid particles of the aluminosilicate and matrix material can be physically admixed. Typically, such aluminosilicate composition can be pelletized or extruded into useful shapes. The crystalline aluminosilicate content can vary anywhere from a few up to 100 wt.% of the total composition. Typical catalytic compositions contain about 1 wt.% to about 100 wt.% crystalline aluminosilicate material and preferably contain about 2 wt.% to about 80 wt.% of such material.

Catalytic compositions comprising the crystalline aluminosilicate material of this invention and a suitable matrix material can be formed by adding a finely-divided crystalline aluminosilicate and a catalytically active metal compound to an aqueous sol or gel of the matrix material. The resulting mixture is thoroughly blended and gelled typically by adding a material such as aqueous ammonia. The resulting gel can be dried and calcined to form a composition in which the crystalline aluminosilicate and catatytically active metal compound are distributed throughout the matrix material.

The ferrierite crystalline aluminosilicates prepared according to this invention are useful as catalysts for various hydrocarbon conversion processes and are suitable for chemical adsorption. Some of the hydrocarbon conversion processes for which the aluminosilicates appear to have useful catalytic properties are fluidized catalytic cracking; hydrocracking; isomerization of normal paraffins and naphthenes; reforming of naphthas and gasoline-boiling-range feedstocks; isomerization of alkylaromatics, such as xylenes; disproportionation of aromatics, such as toluene, to form mixtures of other more valuable products including benzene, xylene, and other higher methyl substituted benzenes; hydrotreating; alkylation, including (a) alkylation of benzene with ethylene, ethanol or other ethyl carbocation precursor to yield ethylbenzene, (b) alkylation of benzene or toluene with methanol or other methanol or carbocation precursor to yield xylenes, especially p-xylene, or pseudocumene, (c) alkylation of benzene with propylene and (d) alkylation of $C_3$ to $C_5$ paraffins with $C_5$ to $C_3$ olefins; hydrodealkylation; hydrodesulfurization; and hydrodenitrogenation. They are particularly suitable for the isomerization of alkylaromatics, such as xylenes, and for the conversion of ethylbenzene. Such aluminosilicates, in certain ion-exchanged forms, can be used to convert alcohols, such as methanol, to hydrocarbon products, such as aromatics or olefins.

The ferrierite composition prepared by this invention is especially suitable for hydrocarbon isomerization and disproportionation. It is especially useful for liquid or vapor phase isomerization of xylenes and particularly the isomerization of mixed xylenes to paraxylene products. Operating conditions for the isomerization of a xylene feed broadly comprise a temperature of about 95° C. to about 540° C., a hydrogen-to-hydrocarbon mole ratio of about 0 to about 20, a weight hourly space velocity (WHSV) of about 0.01 weight unit of feed per hour per weight unit of catalyst (hr.$^{-1}$) to about 90 hr.$^{-1}$, and a pressure of about 0 psig to about 1000 psig. Advantageously, the conditions comprise a temperature of about 250° C. to about 480° C., a hydrogen-to-hydrocarbon mole ratio of about 1 to about 12, a WHSV of about 1 hr.$^{-1}$ to about 20 hr.$^{-1}$, and a pressure of about 0 psig to about 500 psig. The preferred conditions for the isomerization of xylenes comprise a temperature of about 315° C. to about 455° C., a hydrogen-to-hydrocarbon mole ratio of about 2 to about 8, a WHSV of about 1 hr.$^{-1}$ to about 10 hr.$^{-1}$, and a pressure of about 0 psig to about 300 psig. The choice of catalytically active metals to be placed on the crystalline aluminosilicate can be selected from any of those well known in the art. Nickel, molybdenum, and platinum seem to be especially appropriate for isomerzation of aromatics. When used as a catalyst in isomerization processes with suitable catalytically-active materials placed on the crystalline aluminosilicate, good selectivities for production of desired isomers are obtained.

When the ferrierite crystalline aluminosilicate is used as a hydrocracking catalyst, hydrocracking charge stocks can pass over the catalyst at temperatures anywhere from about 260° C. to about 455° C. or higher using known molar ratios of hydrocarbon to hydrogen and varying pressures anywhere from a few up to many thousands of pounds per square inch or higher. The weight hourly space velocity and other process parameters can be varied consistent with the well-known teachings of the art.

The ferrierite crystalline aluminosilicate also is suitable as a reforming catalyst to be used with the appropriate hydrogenation components at well-known reforming conditions including temperatures ranging from about 260° C. to 565° C. or more, pressures anywhere from a few up to 300 psig to 1000 psig, and weight hourly space velocities and hydrogen-to-hydrocarbon mole ratios consistent with those well known in the art.

The ferrierite crystalline aluminosilicates also can be used as adsorbents to absorb selectively specific isomers or hydrocarbons in general from a liquid or vapor stream.

The following Examples demonstrate but do not limit the present invention.

EXAMPLE I

Samples of crystalline aluminosilicate were prepared by dissolving 44.0 grams of sodium aluminate and 34.0 grams sodium hydroxide in 1200 grams distilled water followed by 80.1 grams of 2,4-pentanedione. At this point the pH was adjusted to 12.6–12.7 with NaOH or NaHCO$_3$. To this solution, 480 grams of Ludox HS-40 were added with vigorous stirring continuing for about 15 minutes after addition. The resulting curdy, gelatinous mixture was placed in a stirred, sealed crystallization vessel and heated to 165° C. for three days. The resulting crystalline material was recovered by filtration, washed thoroughly with distilled water, and dried in a forced draft oven at 165° C. for 16 hours. The dried material was program calcined consisting of four hours from 329° F. (165° C.) to 1,100° F. (593° C.), four hours at 1,100° F. (593° C.), and at least four hours from 1,100° F. (593° C.) to 200° F. (93° C.). An x-ray diffraction spectrum of each preparation was checked and showed lines corresponding to those specified in Table I.

Thirty grams of sieve prepared in Example I, identified as a ferrierite-like material, were exchanged twice with ammonium acetate. Each exchange was for 2.0 hours at 90° C. with 450 ml of a 1.7 M aqueous ammonium acetate solution. After each exchange the sieve was filtered from the exchange solution, washed with approximately 1 liter distilled water, and dried on the filter in preparation for transfer to an exchange flask for the next exchange. After the second exchange, the sieve was washed and then dried overnight in a forced draft oven at 165° C. The dried sieve was then program calcined at 1000° F. with a program consisting of (a) linearly increasing the calcination temperature from 329° F. to 1000° F. in 4.0 hours, (b) holding the temperature at 1000° F. for 4 hours, and (c) reducing the calcination temperature at a maximum rate of 200° F. per hour from 1000° F. to 200° F. The catalyst was prepared by dispersing the above calcined and exchanged sieve in PHF-alumina which is initially an acetic acid stabilized alumina hydrosol containing about 10% $Al_2O_3$. To 10.0 grams of calcined and exchanged sieve was added sufficient distilled water to fill sieve pores. The wet sieve was then added and thoroughly mixed with 56.0 grams of alumina hydrosol. The mixture was gelled (solidified) with addition of 9.5 milliliters of concentrated aqueous ammonia. The resulting solid was dried overnight in a forced air oven at 165° C. The dried solid was program calcined at 1000° F. with the program as described above. The calcined solid was crushed and sized to 30 to 50 mesh (U.S. Sieve Series). One gram of the 30-50 mesh catalyst was placed in a micro aromatics test unit, and preconditioned for one hour at 600° F. and 150 psig with 0.3 SCF per hour of hydrogen. The xylene isomerization test results are shown in Table II.

TABLE II

| | | Example I Test Runs | | |
|---|---|---|---|---|
| | | 1 | 2 | 3 |
| Conditions | | | | |
| Reactor Temp. (°C.) | | 383 | 427 | 449 |
| Reactor Pressure (psig) | | 150 | 150 | 150 |
| Space Velocity (WHSV, $hr^{-1}$) | | 6.02 | 5.65 | 6.00 |
| Hydrogen/hydrocarbon (molar ratio) | | 6.26 | 6.66 | 6.28 |
| Contact Time (seconds) | | 2.88 | 2.72 | 2.62 |
| Components (wt. %) | Feed | | | |
| Paraffins and Naphthenes | 0.06 | 0.11 | 0.22 | 0.25 |
| Benzene | 0.04 | 2.01 | 4.04 | 4.56 |
| Toluene | 0.08 | 0.59 | 1.48 | 2.02 |
| Ethylbenzene | 13.1 | 10.4 | 7.09 | 5.40 |
| p-Xylene | 10.9 | 18.7 | 20.0 | 20.0 |
| m-Xylene | 53.6 | 45.7 | 44.3 | 44.8 |
| o-Xylene | 22.1 | 20.8 | 20.4 | 20.4 |
| $C_9^+$ | 0.04 | 1.74 | 2.85 | 2.67 |
| Results[1] | | | | |
| PATE - p-Xylene | | 84.9 | 101.6 | 100.9 |
| m-Xylene | | 87.1 | 97.9 | 92.1 |
| o-Xylene | | 77.2 | 118.1 | 149.3 |
| Ethylbenzene conversion (%) | | 24.2 | 48.4 | 60.7 |
| Xylene Loss (%) | | 1.8 | 2.4 | 1.8 |

[1] PATE = Percent Approach to Theoretical Equilibrium

EXAMPLES II-VII

Five additional samples of ferrierite crystalline aluminosilicate molecular sieve and one sample of mordenite crystalline aluminosilicate molecular sieve were prepared in a manner similar to that described for Example I. Details of these preparations are summarized in Table III. Catalyst compositions were prepared from these samples and tested using procedures similar to that described for Example I. Results of these tests are summarized in Tables IV-IX. The catalyst prepared from the molecular sieve of Example V also was impregnated with 1.2% platinum by adding a solution of 0.0407 grams of tetraamine-platinum (II) chloride in four grams of water to 2.0 grams of catalyst composition by the incipient wetness method. The platinum-impregnated catalyst is designated Example VI. The catalyst compositions prepared from the molecular sieves prepared in Examples II-VII had BET surface areas of 300-380 square meters per gram, pore volumes (600-10 Å radius) of 0.240-0.320 cubic centimeters per gram and an average pore radius of 28-34 angstroms.

TABLE III

| | Examples | | | | |
|---|---|---|---|---|---|
| | II | III | IV | V | VII |
| Reagents | | | | | |
| Water (grams) | 1200 | 1203 | 1000 | 1200 | 1200 |
| Sodium Hydroxide (grams) | 14.8 | 21.0 | 44.2 | 12.0 | 32.4 |
| Sodium Aluminate ($NaAlO_2 \cdot 3/2\ H_2O$) (grams) | 23.0 | 21.4 | 33.6 | 23.0 | 21.8 |
| 2,4-pentanedione (grams) | 28.1 | 46.5 | 106.1 | 28.3 | 77.3 |
| pH | — | 12.75 | 12.5 | — | 12.7 |
| Ludox HS-40 (grams) | 240 | 241.3 | 480.3 | 240 | 241.7 |
| pH after Ludox addition | — | 12.65 | 12.4 | 12.65 | 12.6 |
| Conditions | | | | | |
| Digestion Time (days) | 7 | 3 | 3 | 7 | 8 |
| Digestion Temperature (°C.) | 165 | 165 | 165 | 165 | 165 |
| Product | Ferrierite | Ferrierite | Ferrierite | Ferrierite with minor Mordenite | Mordenite |
| Unit Cell Formula of Ammonium-Exchanged and Calcined Sieve | | | | | |
| Na | — | — | 0.1 | 0.2 | |
| $NH_4$ | — | — | — | 1.1 | |
| H | — | 3.7 | 2.9 | 1.5 | |
| Al | — | 3.7 | 3.0 | 2.8 | |
| Si | — | 32.3 | 33.0 | 33.2 | |
| O | — | 72 | 72 | 72 | |

TABLE IV

| | | Example II Test Runs | | |
|---|---|---|---|---|
| | | 1 | 2 | 3 |
| Conditions | | | | |
| Reactor Temp. (°F.) | | 760 | 800 | 840 |
| Reactor Pressure (psig) | | 150 | 150 | 150 |
| Space Velocity (WHSV, $hr^{-1}$) | | 6.45 | 6.18 | 6.30 |
| Hydrogen/hydrocarbon (molar ratio) | | 5.90 | 6.16 | 6.04 |
| Components (wt. %) | Feed | | | |
| Paraffins and Naphthenes | 0.05 | 0.07 | 0.08 | 0.11 |
| Benzene | 0.08 | 1.28 | 2.81 | 4.25 |
| Toluene | 0.12 | 0.23 | 0.43 | 0.75 |
| Ethylbenzene | 18.8 | 17.1 | 14.5 | 12.2 |
| p-Xylene | 10.3 | 16.8 | 18.4 | 18.9 |
| m-Xylene | 46.6 | 43.4 | 42.1 | 41.9 |
| o-Xylene | 21.9 | 20.3 | 19.4 | 19.1 |
| $C_9^+$ | 0.13 | 0.82 | 1.95 | 2.75 |
| Results[1] | | | | |
| PATE - p-Xylene | | 75.9 | 95.7 | 102.9 |
| m-Xylene | | 79.9 | 93.3 | 93.8 |
| o-Xylene | | 65.3 | 102.7 | 134.0 |
| Ethylbenzene conversion (%) | | 9.10 | 23.14 | 34.95 |
| Xylene Loss (%) | | 0.38 | 1.12 | 1.13 |

[1] PATE = Percent Approach to Theoretical Equilibrium

TABLE V

| | | Example III Test Runs | | |
|---|---|---|---|---|
| | | 1 | 2 | 3 |
| Conditions | | | | |
| Reactor Temp. (°C.) | | 383 | 427 | 449 |
| Reactor Pressure (psig) | | 150 | 150 | 150 |
| Space Velocity (WHSV, hr$^{-1}$) | | 5.81 | 6.24 | 6.79 |
| Hydrogen/hydrocarbon (molar ratio) | | 6.55 | 6.10 | 5.61 |
| Contact time (seconds) | | 2.87 | 2.66 | 2.55 |
| Components (wt. %) | Feed | | | |
| Paraffins and Naphthenes | — | — | — | — |
| Benzene | 0.04 | 0.05 | 0.16 | 0.27 |
| Toluene | 0.07 | 0.10 | 0.13 | 0.16 |
| Ethylbenzene | 18.7 | 18.8 | 18.7 | 18.5 |
| p-Xylene | 8.88 | 8.58 | 9.63 | 10.4 |
| m-Xylene | 47.8 | 48.3 | 47.3 | 46.8 |
| o-Xylene | 24.3 | 24.0 | 24.0 | 23.8 |
| C$_9$+ | 0.14 | 0.16 | 0.14 | 0.18 |
| Results[1] | | | | |
| PATE - p-Xylene | | −2.8 | 7.6 | 14.7 |
| m-Xylene | | −10.7 | 8.1 | 17.1 |
| o-Xylene | | 5.4 | 7.0 | 11.5 |
| Ethylbenzene conversion (%) | | −0.37 | 0.16 | 1.4 |
| Xylene Loss (%) | | 0.16 | 0.18 | 0.11 |

[1]PATE = Percent Approach to Theoretical Equilibrium

TABLE VI

| | | Example IV Test Runs | | |
|---|---|---|---|---|
| | | 1 | 2 | 3 |
| Conditions | | | | |
| Reactor Temp. (°C.) | | 382 | 427 | 449 |
| Reactor Pressure (psig) | | 150 | 150 | 150 |
| Space Velocity (WHSV, hr$^{-1}$) | | 6.39 | 6.30 | 6.36 |
| Hydrogen/hydrocarbon (molar ratio) | | 5.90 | 5.94 | 5.93 |
| Contact time (seconds) | | 2.86 | 2.68 | 2.60 |
| Components (wt. %) | Feed | | | |
| Paraffins and Naphthenes | 0.05 | 0.05 | 0.08 | 0.04 |
| Benzene | 0.04 | 0.05 | 0.10 | 0.13 |
| Toluene | 0.09 | 0.09 | 0.10 | 0.10 |
| Ethylbenzene | 14.1 | 14.3 | 14.1 | 14.2 |
| p-Xylene | 9.85 | 10.7 | 11.2 | 11.8 |
| m-Xylene | 52.8 | 51.5 | 51.1 | 50.5 |
| o-Xylene | 23.1 | 23.3 | 23.3 | 23.2 |
| C$_9$+ | 0.06 | 0.06 | 0.05 | 0.04 |
| Results[1] | | | | |
| PATE - p-Xylene | | 8.8 | 13.3 | 19.2 |
| m-Xylene | | 15.3 | 19.2 | 26.1 |
| o-Xylene | | −10.0 | −9.2 | −10.4 |
| Ethylbenzene conversion (%) | | −1.4 | −0.36 | −0.78 |
| Xylene Loss (%) | | 0.26 | 0.16 | 0.21 |

[1]PATE = Percent Approach to Theoretical Equilibrium

TABLE VII

| | | Example V Test Runs | | |
|---|---|---|---|---|
| | | 1 | 2 | 3 |
| Conditions | | | | |
| Reactor Temp. (°C.) | | 382 | 427 | 449 |
| Reactor Pressure (psig) | | 150 | 150 | 150 |
| Space Velocity (WHSV, hr$^{-1}$) | | 6.39 | 6.18 | 6.30 |
| Hydrogen/hydrocarbon (molar ratio) | | 5.96 | 6.16 | 6.04 |
| Contact time (seconds) | | 2.84 | 2.67 | 2.58 |
| Components (wt. %) | Feed | | | |
| Paraffins and Naphthenes | 0.05 | 0.04 | 0.08 | 0.11 |
| Benzene | 0.08 | 0.66 | 2.81 | 4.24 |
| Toluene | 0.12 | 0.18 | 0.43 | 0.75 |
| Ethylbenzene | 18.8 | 18.00 | 14.45 | 12.23 |
| p-Xylene | 10.3 | 15.33 | 18.35 | 18.91 |
| m-Xylene | 48.6 | 44.57 | 42.05 | 41.89 |
| o-Xylene | 21.9 | 20.74 | 19.44 | 19.09 |
| C$_9$+ | 0.13 | 0.49 | 1.96 | 2.75 |
| Results[1] | | | | |
| PATE - p-Xylene | | 57.8 | 95.7 | 102.8 |
| Ethylbenzene conversion (%) | | 4.3 | 23.1 | 35.0 |

[1]PATE = Percent Approach to Theoretical Equilibrium

TABLE VIII

| | | Example VI Test Runs | | |
|---|---|---|---|---|
| | | 1 | 2 | 3 |
| Conditions | | | | |
| Reactor Temp. (°C.) | | 382 | 427 | 449 |
| Reactor Pressure (psig) | | 150 | 150 | 150 |
| Space Velocity (WHSV, hr$^{-1}$) | | 4.51 | 5.04 | 4.93 |
| Hydrogen/hydrocarbon (molar ratio) | | 8.4 | 8.8 | 9.0 |
| Contact Time (seconds) | | 2.96 | 2.39 | 2.32 |
| Components (wt. %) | Feed | | | |
| Paraffins and Naphthenes | 0.06 | 26.23 | 7.58 | 1.98 |
| Benzene | 0.06 | 3.35 | 7.56 | 9.51 |
| Toluene | 0.11 | 1.11 | 2.53 | 3.13 |
| Ethylbenzene | 20.32 | 9.04 | 10.93 | 6.26 |
| p-Xylene | 14.34 | 13.32 | 20.06 | 18.60 |
| m-Xylene | 41.47 | 31.32 | 29.54 | 40.45 |
| o-Xylene | 23.49 | 14.34 | 20.36 | 18.33 |
| C$_9$+ | 0.15 | 1.31 | 1.45 | 1.94 |
| Results[1] | | | | |
| PATE - p-Xylene | | 67.6 | 170.7 | 99.7 |
| Ethylbenzene conversion (%) | | 55.5 | 46.2 | 69.2 |

[1]PATE = Percent Approach to Theoretical Equilibrium

TABLE IX

| | | Example VII Test Runs | | |
|---|---|---|---|---|
| | | 1 | 2 | 3 |
| Conditions | | | | |
| Reactor Temp. (°C.) | | 382 | 427 | 449 |
| Reactor Pressure (psig) | | 150 | 150 | 150 |
| Space Velocity (WHSV, hr$^{-1}$) | | 6.08 | 5.96 | 6.14 |
| Hydrogen/hydrocarbon (molar ratio) | | 6.20 | 6.32 | 6.14 |
| Contact time (seconds) | | 2.88 | 2.71 | 2.61 |
| Components (wt. %) | Feed | | | |
| Paraffins and Naphthenes | 0.03 | 0.03 | 0.03 | 0.03 |
| Benzene | 0.05 | 0.06 | 0.32 | 0.67 |
| Toluene | 0.10 | 0.12 | 0.66 | 1.77 |
| Ethylbenzene | 17.6 | 17.3 | 16.8 | 15.7 |
| p-Xylene | 10.5 | 10.8 | 15.3 | 17.4 |
| m-Xylene | 50.6 | 50.6 | 45.8 | 42.8 |
| o-Xylene | 21.0 | 21.0 | 20.3 | 19.1 |
| C$_9$+ | — | 0.11 | 0.81 | 2.41 |
| Results[1] | | | | |
| PATE - p-Xylene | | 3.4 | 56.7 | 86.6 |
| m-Xylene | | 2.8 | 57.0 | 78.6 |
| o-Xylene | | 6.6 | 54.1 | 175. |
| Ethylbenzene conversion (%) | | 1.9 | 4.8 | 10.7 |
| Xylene Loss (%) | | −0.36 | 0.83 | 3.4 |

[1]PATE = Percent Approach to Theoretical Equilibrium

I claim:

1. A method to prepare a crystalline aluminosilicate comprising (1) forming an aqueous mixture of an oxide of aluminum, an oxide of silicon, a metal cation and a beta-diketone, (2) maintaining the pH of such mixture between about 9 and about 14 and (3) crystallizing such mixture.

2. The method of claim 1 wherein the crystalline aluminosilicate is ferrierite-like.

3. The method of claim 1 wherein the beta-diketone is 2,4-pentanedione.

4. The method of claim 1 wherein the oxide of aluminum is sodium aluminate.

5. The method of claim 2 wherein the composition of the mixture of initial reactants in terms of mole ratios is:

| | |
|---|---|
| $SiO_2/Al_2O_3$ | 2-240 |
| R/Si | 0.01-1.0 |
| $M^{n+}/Al$ | 0.1-100 |
| R/Al | 0.01-120 |
| $H_2O/Si$ | 5-100 | wherein R is an organic compound and M is at least one cation having a valence n.

6. The method of claim 2 wherein the composition of the mixture of initial reactants in terms of mole ratios is:

| | |
|---|---|
| $SiO_2/Al_2O_3$ | 10-80 |
| R/Si | 0.1-0.5 |
| $M^{n+}/Al$ | 1-10 |
| R/Al | 0.5-20 |
| $H_2O/Si$ | 10-40 | wherein R is an organic compound and M is at least one cation having a valence n.

7. The method of claim 2 wherein the pH of the mixture is maintained between about 12.4 and about 12.8.

8. The method of claim 2 wherein the crystallizing mixture is maintained at about 100° C. to about 250° C. for about 0.25 to about 20 days.

9. The method of claim 2 wherein the crystallizing mixture is maintained at about 125° C. to about 200° C. for about two to about five days.

10. The method of claim 6 wherein M is an alkali-metal or alkaline-earth-metal cation.

11. The method of claim 1 wherein the oxide of silicon is a silicic acid polymer.

12. The method of claim 2 wherein a catalytically active ion or compound is placed onto the ferrierite crystalline aluminosilicate.

13. The method of claim 12 wherein he catalytically active ion is exchanged onto the ferrierite crystalline aluminosilicate.

14. The method of claim 13 wherein the cataytically active ion is hydrogen, metal ions of Groups IB, IIB, IIIA or VIII or of manganese, vanadium, chromium, uranium or rare earth elements.

15. The method of claim 14 wherein the ion is nickel ion.

16. The method of claim 12 wherein a catalytically active compound is impregnated onto the ferrierite crystalline aluminosilicate.

17. The method of claim 16 wherein the cataytically active compound is a water soluble salt of hydrogen, metals of Groups IB, IIB, IIIA, IVB, VB, VIB, VIIB or VIII, or rare earth elements.

18. The method of claim 17 wherein the catalytically active compound is a salt of platinum.

19. The method of claim 2 wherein the prepared ferrierite molecular sieve is incorporated within a suitable matrix material.

20. The method of claim 19 wherein the matrix material is silica, silica-alumina or alumina.

21. The method of claim 1 wherein the crystalline aluminosilicate is mordenite-like.

* * * * *